United States Patent [19]

Evans et al.

[11] 4,327,099
[45] Apr. 27, 1982

[54] PYRANO DERIVATIVES, A PROCESS FOR THEIR PREPARATION AND THEIR USE

[75] Inventors: John M. Evans, Roydon; Roger E. Markwell, Great Dunmow, both of England

[73] Assignee: Beecham Group Limited, England

[21] Appl. No.: 229,190

[22] Filed: Jan. 28, 1981

[30] Foreign Application Priority Data

Feb. 2, 1980 [GB] United Kingdom ............. 3595/80

[51] Int. Cl.$^3$ ............. A61K 31/435; A61K 31/415; C07D 487/00; C07D 235/02
[52] U.S. Cl. ............................ 424/256; 424/273 B; 546/199; 548/305; 548/326
[58] Field of Search ............. 546/199; 548/305, 326; 424/256, 273 B

[56] References Cited

FOREIGN PATENT DOCUMENTS 1495526 4/1977 United Kingdom .
1511187 4/1978 United Kingdom .

OTHER PUBLICATIONS

Chem. Abstracts 65:7130d.
Chem. Abstracts 74:22758h.

Primary Examiner—Ethel G. Love
Attorney, Agent, or Firm—Jacobs & Jacobs

[57] ABSTRACT

Compounds of the formula (I):

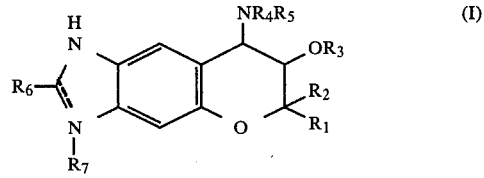

wherein
  $R_1$ and $R_2$ are independently selected from a hydrogen atom and a $C_{1-3}$ alkyl group;
  $R_3$ is a hydrogen atom, a $C_{1-3}$ alkyl or $C_{2-4}$ acyl group;
  $R_4$ is a hydrogen atom or $C_{1-5}$ alkyl group;
  $R_5$ is a $C_{1-5}$ alkyl group, a straight chain $C_{1-3}$ alkyl group terminally substituted by a chlorine atom;
or
  $R_4$ and $R_5$ are joined so that together with the nitrogen atom to which they are attached they form a 5-, 6- or 7-membered ring optionally containing an oxygen or sulphur atom;
  $R_6$ is a hydrogen atom, or a $C_{1-5}$ alkyl, phenyl, $CF_3$ or XH group wherein X is an oxygen or sulphur atom, the dotted line represents a bond, and $R_7$ is not present; or $R_6$ is an oxygen atom joined to the ring carbon atom by a double bond, the dotted line is not present, and $R_7$ is hydrogen;
  the $NR_4R_5$ and $OR_3$ moieties are trans; and pharmaceutically acceptable salts thereof having antihypertensive activity, processes for their preparation and their use in compositions.

10 Claims, No Drawings

PYRANO DERIVATIVES, A PROCESS FOR THEIR PREPARATION AND THEIR USE

This invention relates to novel compounds having blood pressure lowering activity, to a process for their preparation, and to pharmaceutical compositions containing them.

U.K. Pat. Nos. 1,495,526 and 1,511,187 disclose that derivatives of trans-3-hydroxy-4-aminochroman have blood pressure lowering activity.

A structurally distinct group of compounds have now been found that also possess good blood pressure lowering activity with fewer unwanted cardiac effects.

Accordingly, the present invention provides a compound of the formula (I):

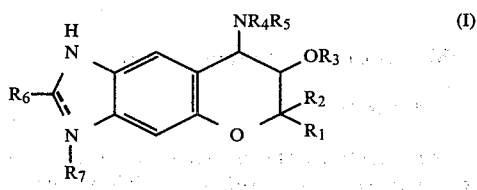

wherein
$R_1$ and $R_2$ are independently selected from a hydrogen atom and a $C_{1-3}$ alkyl group;
$R_3$ is a hydrogen atom, a $C_{1-3}$ alkyl or $C_{2-4}$ acyl group;
$R_4$ is a hydrogen atom or $C_{1-5}$ alkyl group;
$R_5$ is a $C_{1-5}$ alkyl group, a straight chain $C_{1-3}$ alkyl group terminally substituted by a chlorine atom; or
$R_4$ and $R_5$ are joined so that together with the nitrogen atom to which they are attached they form a 5-, 6- or 7-membered ring optionally containing an oxygen or sulfur atom;
$R_6$ is a hydrogen atom, or a $C_{1-5}$ alkyl, phenyl, $CF_3$ or XH group wherein X is an oxygen or sulphur atom, the dotted line represents a bond, and $R_7$ is not present; or $R_6$ is an oxygen atom joined to the ring carbon atom by a double bond, the dotted line is not present, and $R_7$ is hydrogen;
the $NR_4R_5$ and $OR_3$ moieties are trans; and pharmaceutically acceptable salts thereof.

Suitably $R_1$ is a hydrogen atom or a methyl or ethyl group. Most suitably $R_1$ is a methyl group. Suitably $R_2$ is a hydrogen atom or a methyl or ethyl group. Most suitably $R_2$ is a methyl group.

Apt values for $R_3$ include the hydrogen atom, the methyl and ethyl groups, and the acetyl group. Particularly apt values for $R_3$ include the hydrogen atom and the methyl group. A favoured value for $R_3$ is the hydrogen atom.

Suitable acyclic values for the $NR_4R_5$ moiety include those wherein $R_4$ is a hydrogen atom or methyl group and $R_5$ is a $C_{1-5}$ alkyl group. Specific values for acyclic $NR_4R_5$ moieties include dimethylamino, isopropylamino and t-butylamino.

Suitable cyclic values for the $NR_4R_5$ moiety include those of the sub-formula (a):

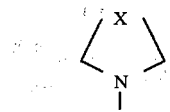

wherein X is a bond, a methylene group, an ethylene group, an ethylidene group, an oxygen or a sulphur atom. Most suitably X is a bond or a methylene group.

When $R_6$ is $C_{1-5}$ alkyl, phenyl, $CF_3$ or XH as defined, then particularly suitable examples include methyl, ethyl; phenyl; $CF_3$; OH or SH.

Suitable salts of the compounds of this invention include acid addition salts with pharmaceutically acceptable inorganic or organic acids such as hydrochloric, hydrobromic, phosphoric, sulphuric, toluene sulphonic, methane, sulphoic, acetic, propionic, succinic, citric, lactic, tartaric, maleic, mandelic or like acids.

From the aforesaid it will be appreciated that a favourable sub-group of compounds of the formula (I) is of formula (II):

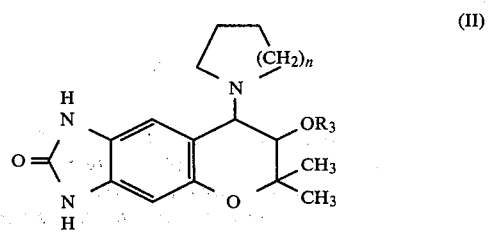

wherein n is 1 or 2, $R_3$ is as hereinbefore defined, and the cyclic amino and $OR_3$ moieties are trans.

Suitable and preferred examples of $R_3$ are as hereinbefore described with relation to formula (I).

Preferably n is 1.

A particularly suitable compound of this invention therefore is 3,6,7,8-tetrahydro-trans-7-hydroxy-6,6-dimethyl-8-piperidino-pyrano[2,3-f]benzimidazole-2 (1H)-one.

A second favourable sub-group is of formula (III):

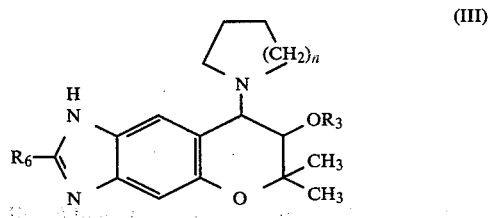

wherein n, $R_3$ and $R_6$ are as hereinbefore defined.

Suitable and preferred examples of $R_3$ are as hereinbefore described with relation in formula (I).

Preferably n is 1.

Very suitable examples of $R_6$ include hydrogen or $C_{1-5}$ alkyl, for example hydrogen.

Another particularly suitable compound of this invention therefore is 3,6,7,8-tetrahydro-trans-7-hydroxy-6,6-dimethyl-8-piperidino-pyrano[2,3-f]benzamidazole.

The invention also provides a process for the preparation of the compounds of formula (I), which process comprises reacting a compound of formula (IV):

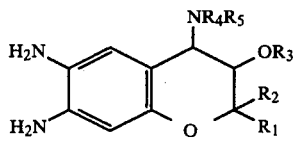 (IV)

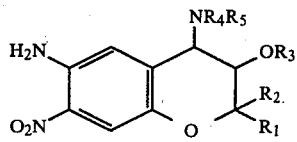 (V)

with a carbonyl or thiocarbonyl source; or with an acid of formula $R^1{}_6CO_2H$ wherein $R^1{}_6$ is hydrogen, $C_{1-5}$ alkyl, $CF_3$ or phenyl.

Reaction with a carbonyl source gives compounds of the formula (I) having the moieties

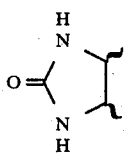

and

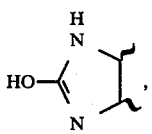, which are of course tautomeric forms. Such reactions maybe effected with for example phosgene and hydrochloric acid, diethyl carbonate, or urea.

Reaction with a thiocarbonyl source gives compounds of the formula (I) having the moiety

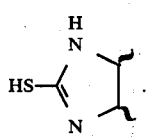.

Such reactions maybe effected with for example carbon disulphide or thiophosgene.

Reaction with the acid $R^1{}_6CO$ H, which is easily achieved with heating, yields compounds of the formula (I) having the moiety

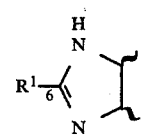

Thereafter if desired a thus formed compound of the formula (I) wherein $R_3$ is hydrogen may be alkylated or acylated in conventional manner to give the corresponding compounds wherein $R_3$ is alkyl and acyl; and salts may be formed.

The compounds of the invention exist in optically active forms. Those skilled in the chemical arts will realise that racemic mixtures of amino compounds can be separated into pure optical isomers using such techniques as fractional crystallisation using optically active acids or the like. All such forms, and mixtures thereof, are covered by this invention.

The intermediates of formula (IV) may be prepared by reduction of a compound of formula (V):

This reduction maybe carried out in any suitable manner, for example by hydrogenation with a palladium catalyst. Also non-hydrogenation reactions maybe used, for example with $SnCl_4$, Sn/HCl, Fe/HCl or the like.

Compounds of formula (V) may be prepared by reacting a compound of formula (VI):

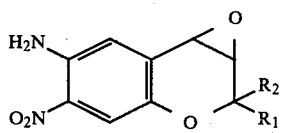 (VI)

with a compound of formula (VII):

HNR_4R_5   (VII)

The reaction of the epoxide may be carried out at any non-extreme low, medium or high temperature (for example, $-10°$ C. to $200°$ C.) but in general ambient or slightly elevated temperatures are most suitable (for example $12°$ to $100°$ C.). The reaction is normally carried out in a solvent such as a lower alcohol or lower ketone, for example methanol, ethanol, propanol, acetone or methylethylketone.

It has been found that the reaction proceeds smoothly if carried out in refluxed ethanol.

The above reaction gives a trans product substantially free of the cis-isomer.

The desired product may be obtained from the reaction mixture by removal of the solvent which is normally accomplished by evaporation under reduced pressure. The initial product may contain some epoxide. This may be separated by dissolving the reaction product in ethyl acetate and extracting into dilute acid. If desired the solvent may be evaporated at this stage but it is usually more convenient to neutralise, back extract into ethyl acetate and recover by evaporation at reduced pressure. If a salt is desired this product (the free base) may be dissolved in diethyl ether containing a little ethanol and treated with a solution of the acid for example in diethyl ether. The desired salt may then be collected by filtration.

In this reaction it may be advisable to protect the 6-amino group, in which case an acyl protecting group such as acetyl is very suitable. This group can readily be removed after the reaction. The epoxides of the formula (VI) may be isolated or used in situ and may be prepared in the general manner described in U.K. Pat. No. 1,495,526.

In a further aspect the present invention also provides a pharmaceutical composition which comprises a compound of this invention and a pharmaceutically acceptable carrier.

The compositions of this invention are most suitably adapted for oral administration although adaption for other modes of administration for example by injection, are also possible.

In order to obtain consistency of administration it is preferred that the compositions of this invention are in the form of a unit-dose. Suitable unit dose forms include tablets, capsules, ampoules and powders in sachets. Such unit dose forms aptly contain from 1 to 100 mg of the compound of this invention and more usually from 2 to 15 mg, for example 5 to 50 mg. Such compositions may be administered from 1 to 6 times a day, more usually from 2 to 4 times a day, in a manner such that the daily dose is from 5 to 200 mg for a 70 kg human adult and more aptly from 10 to 100 mg.

Shaped compositions are favoured composition aspects.

The compositions of this invention may be formulated in conventional manner, for example in a manner similar to that used for known antihypertensive agents such as hydrallazine.

In addition such compositions may contain fruther active agents such as other anti-hypertensive agents especially β-blocking agents, and diuretics.

The invention further provides a method of treatment or prophylaxis of hypertension in mammals including man which comprises the administration of an effective amount of a compound of formula (I) or a pharmaceutically acceptable salt thereof.

The following Examples illustrate the invention.

EXAMPLE 1

(a)

6-Acetamido-3,4-dihydro-2,2-dimethyl-7-nitro-trans-4-piperidino-2H-benzo[b]pyran-3-ol To 6-acetamido-2,2-dimethyl-7-nitro-2H-benzo[b]pyran (10.78 g) dissolved in dimethyl sulphoxide (100 ml) containing water (1.48 ml) was added freshly recrystallised N-bromosuccinimide (14.59 g) with vigorous stirring. Dilution with water (700 ml) and filtration and drying of the solid obtained gave 6-acetamido-trans-3-bromo-3,4-dihydro-2,2-dimethyl-7-nitro-2H-benzo[b]pyran-4-ol as a yellow solid (14.06 g). A small portion recrystallised from ethanol had mp 198°–200° C.;

n.m.r. (CDCl$_3$/DMSOd$_6$): δ1.62 (3H); 1.79 (3H); 2.37 (3H); 4.27 (1 exchangeable H, m) overlapped with 4.35 (1H, d, J=9); 5.01 (1H, d, J=9); 7.83 (1H); 8.56 (1H); 10.02 (1 exchangeable H, m).

Analysis: Calculated for $C_{13}H_{15}N_2O_5Br$: C, 43.47; H, 4.21; N, 7.80. Found: C, 43.70; H, 4.37; N, 7.46%.

This bromohydrin (14.02 g), sodium hydroxide pellets (14.00 g) dioxan (750 ml) and water (140 ml) were stirred at room temperature during 3 hours. Evaporation to half volume and addition of water (1 liter) and extraction via ethyl acetate (3×500 ml), and washing of the combined organic layers with water and brine, drying and solvent removal gave a red gummy solid (11.12 g). Recrystallisation from ethanol gave 6-acetamido-3,4-dihydro-2,2-dimethyl-3,4-epoxy-7-nitro-2H-benzo[b]pyran as a yellow solid (5.92 g) of mp 156°–158° C.

n.m.r. (CDCl$_3$) δ: 1.27 (3H); 1.60 (3H); 2.25 (3H), 3.53 (1H, d J=4); 3.98 (1H, d, J=4); 7.62 (1H); 8.77 (1H); 10.05 (1H).

Manipulation of the mother liquors gave an additional crop of epoxide (0.74 g).

Analysis: Calculated for $C_{13}H_{14}N_2O_5$: C, 56.11; H, 5.07; N, 10.07. Found: C, 55.92; H, 5.27; N, 9.82%

This expoxide (4.40 g) and piperidine (1.60 ml) were refluxed in ethanol (80 ml) for 16 hours. Removal of solvent, addition of ether, washing with water before drying, following by filtration gave the crude free base (3.54 g). Treatment of this crude material (0.70 g) in the minimum volume of ethanol with methane sulphonic acid (0.125 ml) followed by two recrystallisations from ethanol of the crude yellow solid obtained, gave 6-acetamido-3,4-dihydro-2,2-dimethyl-7-nitro-trans-4-piperidino-2H-benzo[b]pyran-3-ol methane sulphonate of mp 200°–204° C.

n.m.r. (DMSOd$_6$): δ1.09 (3H); 1.44 (3H); 1.63 (6H, broad m); 2.05 (3H); 2.43 (3H); 3.55 (6H, broad m, include 2 exchangeable H); 4.20 (1H, d, J=9); 4.67 (1H, d, J=9); 7.41 (1H); 7.98 (1H); 10.17 (1 exchangeable H).

Analysis: Calculated for $C_{19}H_{29}N_3O_8S$: C, 49.66; H, 6.36; N, 9.15; S, 7.00. Found: C, 49.75; H, 6.35; N, 8.97; S, 7.23%.

(b)

6-Amino-3,4-dihydro-2,2-dimethyl-7-nitro-trans-4-piperidino-2H-benzo[b]pyran-3-ol The crude free base (2.84 g, obtained from the reaction of 6-acetamido-3,4-epoxy-3,4-dihydro-2,2-dimethyl-7-nitro-2H-benzo[b]pyran with piperidine in Example 1(a)) and 5 N hydrochloric acid (45 ml) were refluxed in ethanol (80 ml) for 3 hours. Dilution with water, basification and extraction via ethyl acetate, followed by drying and evaporation gave the crude free base as a red foam (2.41 g). Treatment of this material in the minimum volume of ethanol-diethyl ether with methylene sulphonic acid until precipitation had ceased and recrystallisation from ethanol-diethyl ether gave 6-amino-3,4-dihydro-2,2-dimethyl-7-nitro-trans-4-piperidino-2H-benzo[b]pyran-3-ol methane sulphonate as brick red crystals (2.47 g) of mp 243°–244° C.

n.m.r. (DMSOd$_6$): δ1.06 (3H); 1.47 (3H); 1.74 (6H, broad m); 2.49 (3H); 3.30 (4H, broad m); 3.88–4.94 (4H, broad m); overlapped with 4.20 (1H, d, J=8) and 4.59 (1H, d, J=8); 7.42 (1H); 7.62 (1H).

Analysis: Calculated for $C_{17}H_{27}N_3O_7S$: C, 48.92; H, 6.52; N, 10.07; S, 7.71. Found: C, 48.74; H, 6.62; N, 9.72; S, 7.52%.

(c)

6,7-Diamino-3,4-dihydro-2,2-dimethyl-trans-4-piperidino-2H-benzo[b]pyran-3-ol

A solution of 6-amino-3,4-dihydro-2,2-dimethyl-7-nitro-trans-4-piperidino-2H-benzo[b]pyran-3-ol (140 mg) in ethanol (30 ml) was hydrogenated over 5% palladium-charcoal (0.1 g) until uptake of hydrogen ceased. The solution was filtered (Kieselguhr) and evaporated to dryness in vacuo to give unstable 6,7-diamino-3,4-dihydro-2,2-dimethyl-trans-4-piperidino-2H-benzo[b]pyran-3-ol (0.12 g) which was used immediately in the following reactions. Rf (0.3) in ethyl acetate-hexane 1:2 (colourless spot) compared with starting material with Rf (0.6) as an orange spot.

(d)

3,6,7,8-Tetrahydro-trans-7-hydroxy-6,6-dimethyl-8-piperidino-pyrano[2,3-f]benzimidazole-2 (1H)-one hydrochloride (Compound 1)

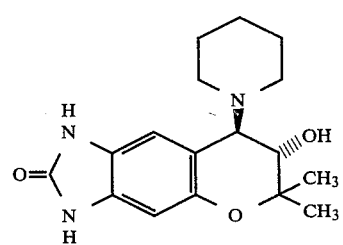

(1)

A solution of 6,7-diamino-3,4-dihydro-2,2-dimethyl-trans-4-piperidino-2H-benzo[b]pyran-3-ol (0.12 g) in 5N-hydrochloric acid (10 ml) was treated with a 12.5% solution of phosgene in toluene (20 ml) and the mixture was stirred at room temperature for 45 minutes. A vigorous stream of nitrogen was then passed through the mixture for 10 minutes, and the solution was evaporated to dryness in vacuo. The residue was recrystallised from ethanol-ether to give the hygroscopic 3,6,7,8-tetrahydro-trans-7-hydroxy-6,6-dimethyl-8-piperidino-pyrano[2,3-f]benzimidazole-2 (1H)-one hydrochloride (1) (0.067 g) mp 177°–180° C.

i.r. (Nujol) $v_{max}$ 3200–3400 (br), and 1700 (NHCONH) cm$^{-1}$.

Mass spectrum: E.I. 317 (M+; 1%); 315 (0.5), 245 (32) M+-C$_4$H$_8$O-Retro Diels-Alder cleavage of O—C$_2$ and C$_3$-C$_4$), 232 (62) 163 (100) and 84 (80).

n.m.r. (D$_2$O): $\delta$1.0 (s); 1.45 (s) and 1.5–2.0(m) (total 15H); 30 (4H, m); 6.7 (1H, s) and 7.26 (1H, s).

The remaining protons are obscured by the D$_2$O peak at ca. 4.8.

EXAMPLE 2

3,6,7,8-Tetrahydro-trans-7-hydroxy-6,6-dimethyl-8-piperidino-pyrano[2,3f]benzimidazole dihydrochloride hydrate:ethanol (1:1) (Compound 2)

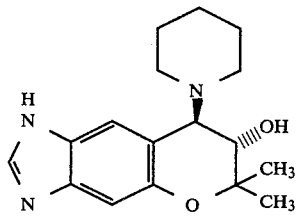

(2)

A solution of 6,7-diamino-3,4-dihydro-2,2-dimethyl-trans-4-piperidino-2H-benzo[b]pyran-3-ol (120 mg) in formic acid (10 ml) was heated under reflux under nitrogen for three hours. The solution was evaporated to dryness in vacuo and the residue was treated with an excess of ethanolic-hydrogen chloride and evaporated to dryness in vacuo. The residue was recrystallised from ethanol-ether to give the hygroscopic 3,6,7,8-tetrahydro-trans-7-hydroxy-6,6-dimethyl-8-piperidino-pyrano[2,3-f]benzimidazole dihydrochloride hydrate:ethanol (1:1) (155 mg) mp 210°–215° C. (dec).

Analysis: Calculated for C$_{17}$H$_{23}$N$_3$O$_2$.2HCl.H$_2$O EtOH: C, 52.05; H, 7.6; N, 9.6; Cl, 16.2. Found: C, 52.65; H, 7.1; N, 9.95; Cl, 16.4%.

I.R. (Nujol) 2300–3550 cm$^{-1}$.

Mass spectrum: E.I. 301 (M+; 3%), 229 (100) (M+—C$_4$H$_8$O—Retro Diels-Alder cleavage of O—C$_2$ and C$_3$-C$_4$), 216 (42), 188 (27), 173 (35), 147 (52), 85 (52), 84 (93) and 83 (80).

n.m.r. (D$_2$O): $\delta$1.0 (s); 1.50 (s) and 1.2–2.0 (m) (total 12H); 3.0 (4H, m); 7.35 (1H, s); 8.1 (1H, s) and 9.1 (1H, s).

The remaining protons are obscured by the D$_2$O peak at ca. 4.8.

DEMONSTRATION OF EFFECTIVENESS

Biological Data

Systolic blood pressures were recorded by a modification of the tail cuff method escribed by J. M. Claxton, M. G. Palfreyman, R. H. Poyser and R. L. Whiting, European Journal of Pharmacology, 37, 179 (1976). An oscilloscope or W+W BP recorder, model 8002, was used to display pulses. Prior to all measurements rats were placed in a heated environment (33.5°±0.5° C.) before transfer to a restraining cage. Each deterministion of blood pressure was the mean of at least 6 readings. Spontaneously hypertensive rats (aged 12–18 weeks) with systolic blood pressure >170 mmHg were considered hypertensive.

| Compound No. | Time Post Dose (hrs) | % Change in Systolic Blood Pressure | % Change in Heart Rate |
|---|---|---|---|
| (1) (1 mg/kg p.o.) | Initial Values | 218 ± 4 | 455 ± 6 |
| | 1 | −2 ± 2 | −1 ± 1 |
| | 2 | −3 ± 1 | −7 ± 1 |
| | 4 | −4 ± 1 | −9 ± 2 |
| | 6 | −10 ± 2 | −6 ± 2 |
| (1) (10 mg/kg p.o.) | Initial Values | 192 ± 3 | 477 ± 6 |
| | 1 | −40 ± 7 | −2 ± 2 |
| | 2 | * | * |
| | 4 | * | * |
| | 6 | −38 ± 10 | −3 ± 2 |
| (2) (1 mg/kg p.o.) | Initial Values | 244 ± 4 | 472 ± 5 |
| | 1 | −6 ± 2 | −5 ± 1 |
| | 2 | −12 ± 3 | −7 ± 1 |
| | 4 | −12 ± 2 | −9 ± 2 |
| | 6 | −13 ± 2 | −6 ± 2 |
| (2) (10 mg/kg p.o.) | Initial Values | 205 ± 2 | 489 ± 4 |
| | 1 | −47 ± 6 | −3 ± 1 |
| | 2 | −64*° | −5*° |
| | 4 | −56*° | −3*° |
| | 6 | −33 ± 6 | −8 ± 3 |

*At 2 and 4 hours rats had no measurable pulses.
°n = 1 - Difficulty with pulses at 2 and 4 hours. Groups of 6 Spontaneously Hypertensive rats were used.

TOXICITY

No toxic effects were observed during these tests.

We claim:

1. A compound of the formula (I):

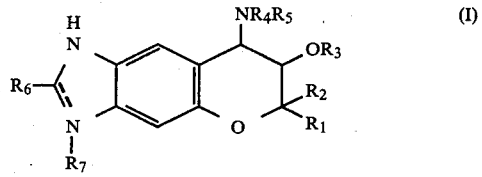

(I)

wherein
R$_1$ and R$_2$ are independently selected from a hydrogen atom and a C$_{1-3}$ alkyl group;
R$_3$ is a hydrogen atom, a C$_{1-3}$ alkyl or C$_{2-4}$ acyl group;
R$_4$ is a hydrogen atom or C$_{1-5}$ alkyl group;
R$_5$ is a C$_{1-5}$ alkyl group, a straight chain C$_{1-3}$ alkyl group terminally substituted by a chlorine atom;
or
R$_4$ and R$_5$ are joined so that together with the nitrogen atom to which they are attached they form pyrrolidyl or piperidinyl;
R$_6$ is a hydrogen atom, or a C$_{1-5}$ alkyl, phenyl, CF$_3$ or XH group wherein X is an oxygen or sulphur atom, the dotted line represents a bond, and R$_7$ is not present; or R$_6$ is an oxygen atom joined to the ring carbon atom by a double bond, the dotted line is not present, and R$_7$ is hydrogen;

the $NR_4R_5$ and $OR_3$ moieties are trans; and pharmaceutically acceptable salts thereof.

2. A compound according to claim 1 wherein $R_1$ and $R_2$ are both methyl.

3. A compound according to claim 1 of the formula (II):

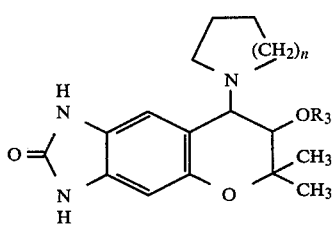

wherein n is 1 or 2, $R_3$ is as defined in claim 1 and the cyclic amino and $OR_3$ moieties are trans.

4. A compound according to claim 1 of the formula (III):

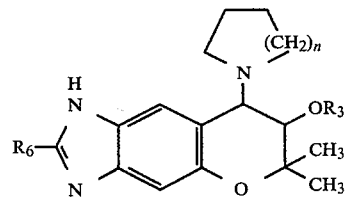

wherein n is 1 or 2 and $R_3$ and $R_6$ are as defined in claim 1.

5. A compound according to claim 4 wherein $R_6$ is hydrogen or $C_{1-6}$ alkyl.

6. A compound according to claim 3 or 4 wherein n is 1.

7. A compound according to claim 1 wherein $R_1$ is hydrogen.

8. 3,6,7,8-tetrahydro-trans-7-hydroxy-6,6-dimethyl-8-piperidino-pyrano[2,3-f]benzimidazole-2 (1H)-one or 3,6,7,8-tetrahydro-trans-7-hydroxy-6,6-dimethyl-8-piperidino-pyrano[2,3-f]benzimidazole.

9. A pharmaceutical composition for treating hypertension, comprising an anti-hypertensive effective amount of a compound according to claim 1 and a pharmaceutically acceptable carrier.

10. A method for the treatment of hypertension in mammals including man, comprising administering to the sufferer an anti-hypertensive effective amount of a compound according to claim 1.

* * * * *